United States Patent
Meiwa et al.

(12) 
(10) Patent No.: US 6,294,509 B1
(45) Date of Patent: *Sep. 25, 2001

(54) DISINTEGRATING PARTICLES AND CLEANSER OR DETERGENT COMPOSITION

(75) Inventors: Zenbei Meiwa; Mamoru Nakamura; Tatsuki Matsumoto; Yoshihiro Hasebe, all of Wakayama; Hideyuki Hanazawa; Ritsuko Yamazaki, both of Tokyo, all of (JP)

(73) Assignee: Kao Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/308,642

(22) PCT Filed: Sep. 25, 1998

(86) PCT No.: PCT/JP98/04294

§ 371 Date: May 28, 1999

§ 102(e) Date: May 28, 1999

(87) PCT Pub. No.: WO99/16856

PCT Pub. Date: Apr. 8, 1999

(30) Foreign Application Priority Data

Sep. 29, 1997 (JP) .................................................. 9-263718

(51) Int. Cl.[7] ............................. C11D 17/06; C11D 3/02; C11D 7/02

(52) U.S. Cl. ......................... 510/130; 510/139; 510/395; 510/438; 510/444; 510/475; 510/507; 510/511; 424/489; 134/42

(58) Field of Search ................................... 510/130, 137, 510/395, 475, 444, 507, 438, 511; 424/489; 134/42

(56) References Cited

U.S. PATENT DOCUMENTS 3,574,823 * 4/1971 Roberts et al. ........................ 424/49
3,645,904 * 2/1972 Beach ................................... 510/139
4,344,930 * 8/1982 Macrae et al. ......................... 424/28
4,414,130 * 11/1983 Cheng .................................... 252/140
4,443,564 * 4/1984 Hauschild et al. .................... 523/105
4,537,604 * 8/1985 Dawson ................................. 51/298
4,582,615 * 4/1986 Ramachandran et al. ............ 252/8.6
4,701,445 * 10/1987 Shull ...................................... 514/57
4,828,721 * 5/1989 Bollier et al. ......................... 252/8.7
5,110,603 * 5/1992 Rau ....................................... 424/466
5,182,103 * 1/1993 Nakane et al. ..................... 424/78.03
5,490,955 * 2/1996 Hagan et al. ...................... 424/70.19
5,871,761 * 2/1999 Kuwata et al. ....................... 424/401
6,037,380 * 3/2000 Venables et al. ..................... 514/781
6,063,366 * 5/2000 Sugai et al. ............................ 424/69
6,106,813 * 8/2000 Mondet et al. ........................ 424/61

FOREIGN PATENT DOCUMENTS 0 104 679-A2 * 8/1984 (EP) .
0 372 427-A2 * 6/1990 (EP) .
0 439 373-A1 * 7/1991 (EP) .
1284545 * 8/1972 (GB) .
58-192814-A * 11/1983 (JP) .
610169897-A * 1/1986 (JP) .
08 208455-A * 8/1996 (JP) .

* cited by examiner

*Primary Examiner*—Lorna M. Douyon
(74) *Attorney, Agent, or Firm*—Oblon, Spivak, McClelland, Maier & Neustadt, P.C.

(57) ABSTRACT

The invention relates to disintegrating particles formed by agglomerating primary particles at least part of which are insoluble in water, wherein the agglomeration of the disintegrating particles is disintegrated in an aqueous solution containing a water-soluble salt by lowering the concentration of the water-soluble salt. The invention also relates to a cleanser or detergent composition that includes the disintegrating particles, a water-soluble salt at a concentration lower than its saturated solubility, a surfactant and water. The composition has excellent physical (mechanical) cleanability and stability with time and gives users a pleasant feeling upon use. The composition does not cause damage to and itch on the skin because the disintegrating particles are disintegrated during cleansing and rinsing, and it is extremely good in rinsability.

23 Claims, No Drawings

DISINTEGRATING PARTICLES AND CLEANSER OR DETERGENT COMPOSITION

TECHNICAL FIELD

The present invention relates to disintegrating particles and a cleaner or detergent composition containing the same, and more particularly to disintegrating particles which disintegrate during cleansing and rinsing, thereby causing little damage to and itchiness of the skin. A cleanser or detergent composition which contains the disintegrating particles has outstanding physical (mechanical) cleaning capability, and has excellent rinsability properties because the particles readily disintegrate during rinsing.

BACKGROUND ART

In recent years, various kinds of rinse-out type skin cleansers (facial soap, body soap, massaging cream and solid soap) have been marketed and used. The reasons for the success of these products is that they provide users with a fresh clean feeling after use and moreover have the desirable property that excess keratin (dirt), clogged skin pores, and the like, which are difficult to remove with the conventional cleanser compositions, can be washed out by virtue of the physical cleansing effects of the rinse-out type skin cleansers.

Controlling the particle diameter and hardness of a scrubbing cleanser in view of problems of irritation to the skin and skin roughness has also been investigated, in order to develop a cleanser having high cleanability that causes little skin irritation (Japanese Patent Application Laid-Open No. 151693/1990).

On the other hand, cleanser compositions have been proposed to achieve high physical detergency and to smoothly finish the skin by incorporating particles of sodium chloride in a proportion not lower than its saturated solubility in the cleanser composition (Japanese Patent Application Laid-Open No. 305951/1994). Other cleanser compositions have been proposed that are intended to achieve high physical detergency and to smoothly finish the skin by incorporating particles of a water-soluble inorganic salt in the cleanser composition and dissolving potassium chloride and magnesium chloride therein with the object of stabilizing the resulting dispersion (Japanese Patent Application Laid-Open No. 208455/1996).

However, the cleanser compositions comprising the scrubbing cleanser wherein the particle diameter and hardness have been controlled still have problems because they leave a feeling of mixed foreign matter upon massaging, and it is difficult to rinse out afterwards.

The cleanser composition in which the particles of sodium chloride are incorporated in a proportion not lower than its saturated solubility have the problems of dispersion stability and dispersibility of individual components including the scrubbing cleanser (scrubber), since the scrubber tends to cause agglomeration and sedimentation. In addition, since sodium chloride is incorporated in a proportion not lower than its saturated solubility, the composition is undesirable because its foamability is extremely reduced upon cleansing, and so its cleaning ability and skin feeling are deteriorated.

On the other hand, in the cleanser composition in which potassium chloride and magnesium chloride are incorporated in addition to the above-described particles of the water-soluble inorganic salt, the agglomeration and sedimentation of the scrubber are improved. However, since the water-soluble inorganic salt is incorporated in a proportion not lower than its saturated solubility, the composition undesirably has a reduced foamability upon cleansing, and so its cleaning ability and skin feel are deteriorated.

DISCLOSURE OF THE INVENTION

One object of the invention is to provide a cleansing composition having high detergency and gives users a pleasant feeling upon use. Another object is to provide a cleansing composition that does not cause damage to and itch on the skin. Another object of the present invention is to provide a cleansing composition having extremely good rinsability because the disintegrating particles are easily disintegrated by either rinse or tears.

These and other objects are achieved by providing disintegrating particles formed by agglomerating primary particles at least part of which are insoluble in water (hereinafter referred to as "disintegrating particles"), wherein the agglomeration of the disintegrating particles disintegrates in an aqueous solution containing a water-soluble salt by lowering the concentration of the water-soluble salt.

According to the present invention, there is also provided a cleanser composition that contains the disintegrating particles, a water-soluble salt, a surfactant and water, wherein the concentration of the water-soluble salt is lower than its saturated solubility.

DETAILED DESCRIPTION OF THE PREFERRED EMBODIMENTS

Other features of the invention will become apparent in the following description of preferred embodiments, which are given for illustration of the invention and are not intended to be limiting thereof.

The disintegrating particles according to the present invention are agglomerated particles formed by agglomerating primary particles at least part of which are insoluble in water, and are such that the agglomeration thereof is disintegrated in an aqueous solution containing a water-soluble salt by lowering in the concentration of the water-soluble salt, namely their rate of disintegration is higher in the case where the concentration of the water-soluble salt is low compared with the case where the concentration is high.

No particular limitation is imposed on the primary particles for forming the disintegrating particles according to the present invention so far as at least a portion of the particles is insoluble in water. Preferable examples thereof include water-insoluble primary particles and a combination of water-insoluble primary particles and water-soluble primary particles. These primary particles may be either organic particles or inorganic particles. The term "water-insoluble" as used herein means that the solubility of the subject particles is lower than 50 wt. %, when 1 part by weight of the particles are dissolved in 99 parts by weight of water, while the term "water-soluble" means that the solubility under the same conditions as described above is at least 50 wt. %. Preferably, the solubility is calculated out from a solids content in a filtrate obtained by filtering the aqueous solution through filter paper (No. 2). The water-soluble primary particles are preferably those such that the solubility is at least 90 wt. %.

Examples of the water-insoluble organic primary particles include primary particles of synthetic polymers, such as polyethylene, polypropylene, polyamide, polyethylene terephthalate, polystyrene, polyurethane, sodium poly(meth)

acrylate, poly(meth)acrylic esters, rubbers such as ethylene rubber, propylene rubber, styrenebutadiene rubber, butadiene rubber and silicone rubber, and crosslinked products thereof; and natural polymers such as cellulose and derivatives thereof, chitosan and derivatives thereof, starch and fruit shells, and derivatives thereof. Among these, the primary particles of polyethylene, polyamide, polystyrene, sodium poly(meth)acrylate, poly(meth)acrylic esters, cellulose and derivatives thereof, and starch are preferably used.

Examples of the water-insoluble primary particles include primary particles of bentonite, talc, mica, kaolin, sepiolite, silica, calcium carbonate, titanium oxide, silicic acid anhydride, hydroxy calcium apatite and pearl powder. Among these, bentonite, talc, mica, kaolin and silica are preferably used.

These water-insoluble primary particles may be in any form of true sphere, substantial sphere and irregular shapes formed by grinding or the like. Hollow or porous particles may also be used. These water-insoluble primary particles may be used either singly or in any combination thereof.

As the water-soluble organic primary particles, there may be used primary particles of synthetic products such as polyvinyl alcohol and derivatives thereof, alkali salts of poly(meth)acrylic acid, alkali salts of (meth)acrylic acid/ (meth)acrylate copolymers, alkali salts of acrylic acid/ maleic acid copolymers, and polyvinyl pyrrolidone; semisynthetic products such as methyl cellulose, ethyl cellulose, sodium carboxymethyl cellulose, hydroxyalkyl cellulose and modified starch (hydroxyalkyl-modified starch, phosphate-modified starch, etc.); and natural products such as starch, sucrose, lactose, seaweeds and proteins.

Examples of the water-soluble inorganic primary particles include primary particles of chlorides such as sodium chloride, potassium chloride and magnesium chloride; sulfates such as sodium sulfate, potassium sulfate, magnesium sulfate and aluminum sulfate; and carbonates such as sodium carbonate and sodium hydrogencarbonate. As the sodium chloride, may be used common salt generally sold, highly purified salt, natural salt and the like. Among these, sodium chloride, potassium chloride, magnesium chloride and sodium carbonate are preferred.

The form of these water-soluble primary particles is also not limited, and they may be used either singly or in any combination thereof.

The weight ratio of the water-insoluble primary particles to the water-soluble primary particles in the disintegrating particles according to the present invention is preferably within a range of from 1/99 to 100/0, more preferably 50/50 to 100/0.

The average particle diameter of these primary particles is preferably 70 μm or smaller, more preferably 60 μm, and most preferably 50 μm or smaller. The fact that the average particle diameter of the primary particles falls within this limit is preferred in that the primary particles give users no feeling of physical disorder and have good rinsability when the disintegrating particles are disintegrated during cleansing of an object to be cleaned or by rinse and tears. The size is measure according to ordinary methods.

The average particle diameter of the disintegrating particles according to the present invention is preferably within a range of from 100 μm to 800 μm, more preferably from 125 μm to 600 μm, most preferably from 150 μm to 360 μm. The fact that the average particle diameter of the disintegrating particles falls within the range of from 100 μm to 800 μm is preferred in that the resulting cleanser composition give users a particularly little feeling of physical disorder upon use and has very low irritativeness to the skin. The size is measured according to ordinary methods.

The disintegrating particles according to the present invention are desirably such that the above-described primary particles are bonded to one another into agglomerates by a water-soluble binder.

No particular limitation is imposed on such a water-soluble binder so far as it is dissolved in an aqueous solution of a water-soluble salt when the salt concentration of the aqueous solution is lowered and deposited when the salt concentration is raised. However, synthetic products such as polyvinyl alcohol and derivatives thereof (for example, itaconic acid-modified polyvinyl alcohol), sulfonic acid-modified polyvinyl alcohol and maleic acid-modified alcohol, alkali salts of poly(meth)acrylic acid, alkali salts of (meth)acrylic acid/(meth)acrylate copolymers, alkali salts of acrylic acid/ maleic acid copolymers, and polyvinyl pyrrolidone; semisynthetic products such as methyl cellulose, ethyl cellulose, sodium carboxymethyl cellulose, hydroxyalkyl cellulose and starch derivatives; and natural polymers such as starch, seaweeds, sticky materials of plants and proteins are used.

In the disintegrating particles according to the present invention, materials used for the water-soluble primary particles and the water-soluble binder may be the same or different from each other.

It is preferable that the water-soluble binder should be used in a proportion of from 0.5 wt. % to 30 wt. % more preferably 0.75–25 wt. %, and most preferably 1–10 wt. %, based on the weight of the primary particles, from the viewpoints of easy disintegration of the resulting disintegrating particles and operating characteristics upon the preparation of the disintegrating particles or the cleanser composition containing the particles.

No particular limitation is imposed on the preparation process of the disintegrating particles according to the present invention. However, the disintegrating particles are preferably prepared, for example, either by mixing the primary particles and the water-soluble binder and granulating the resultant mixture in accordance with a granulation process such as rolling granulation, rolling fluidized granulation, fluidized bed granulation, agitated rolling granulation, melt granulation, extrusion granulation or spray granulation, or a coating process such as spray drying, or by granulating the primary particles in accordance with such a granulation or coating process while mixing the primary particles with the water-soluble binder.

As described above, the thus-obtained disintegrating particles according to the present invention has a feature that the rate of disintegration thereof in an aqueous solution containing the water-soluble salt becomes higher as the concentration of the water-soluble salt is lowered. Accordingly, when the disintegrating particles are incorporated in a cleanser composition, the disintegrating particles are stably dispersed in the cleanser composition without being disintegrated, but they are disintegrated as the concentration of the water-soluble salt is lowered during cleansing and rinsing. Taking such incorporation into the cleanser composition into consideration, it is preferable that the disintegrating characteristics of the disintegrating particles according to the present invention should be designed in such a manner that at least part of the particles are disintegrated in an aqueous solution containing the water-soluble salt at a concentration lower than 1.0 wt. %, preferably lower than 1.5 wt. %. It is more preferable from the viewpoint of rinsability in rinse and tears that the disintegrating characteristics should be designed in such a manner that at least 60 vol. % preferably 70%, and more preferably 80% of the particles are disintegrated in an aqueous solution containing the water-soluble salt at a concentration lower than 1.0 wt. %, preferably lower than 1.5 wt. %. It is also preferable that the particles disintegrated at this time should be reduced to an average particle diameter of 80 μm or smaller, more preferably 70 μm, most preferably 65 μm or smaller.

The cleanser composition according to the present invention comprises the abovedescribed disintegrating particles, a water-soluble salt, a surfactant and water, wherein the concentration of the water-soluble salt is lower than its saturated solubility.

The amount of the disintegrating particles incorporated into the cleanser composition according to the present invention is preferably 1 to 25 wt. %, particularly 2 to 20 wt. % and more preferably 2–15 wt. % from the viewpoints of a feeling upon use and physical (mechanical) cleanability.

The water-soluble salt used in the cleanser composition according to the present invention includes water-soluble inorganic salts and water-soluble organic salts. However, the water-soluble inorganic salts are preferred.

Examples of the water-soluble inorganic salts include chlorides such as sodium chloride, potassium chloride and magnesium chloride; sulfates such as sodium sulfate, potassium sulfate, magnesium sulfate and aluminum sulfate; and carbonates such as sodium carbonate and sodium hydrogencarbonate. As the sodium chloride, may be used common salt generally sold, highly purified salt, natural salt and the like. Among these, sodium chloride, potassium chloride, magnesium chloride and sodium carbonate are particularly preferably used.

Examples of the water-soluble organic salts include acid salts such as citric acid salt, succinic acid salt, maleic acid salt, fumaric acid salt and malic acid salt, as well as anionic surfactants such as various kinds of fatty acid soap, ester type phosphates, acylated amino acid salts, sulfosuccinates and taurate type surfactants. These organic salts may preferably be used in combination with the water-soluble inorganic salt. In this case, a weight ratio of the water-soluble inorganic salt to the water-soluble organic salt is preferably within a range of from 100/0 to 5/95, more preferably 90/10 to 5/95 and most preferably 50/50 to 5/95.

Preferably, the amount of these water-soluble salts incorporated is less than their saturated solubility in water in the cleanser composition. However, from the viewpoints of disintegrating characteristics by rinse and tears and foamability of the resulting cleanser composition, the salts are preferably incorporated in an amount of from at least 1.0 wt. % to less than the saturated solubility, more preferably from at least 1.5 wt. % to less than the saturated solubility, particularly from at least 2.0 wt. % to at most 0.8 times of the saturated solubility.

No particular limitation is imposed on the surfactant used in the cleanser composition according to the present invention. However, examples of a main surfactant include anionic surfactants such as various kinds of fatty acid soap, phosphoric esters, acylated amino acids, sulfosuccinic acids, taurate type surfactants and polyoxyethylene alkyl sulfates; and nonionic surfactants such as alkylsacchrides and ethylene oxide-added surfactants. Among these, the phosphoric esters, acylated amino acids and alkylsaccharides are preferred because of their low irritativeness to the skin.

Incidentally, the surfactants and water-soluble organic salts used in the cleanser composition according to the present invention overlap each other. Any ionic surfactant which functions as a salt may also be used as the water-soluble salt.

No particular limitation is imposed on the amount of such a main surfactant incorporated. However, it is preferable that the surfactant should be incorporated in an amount of 60 to 90 wt. % when the cleanser composition is in the form of solid, 40 to 70 wt. % in the form of paste, 40 to 70 wt. % in the form of gel, or 10 to 50 wt. % in the form of liquid.

Further, an amine oxide or imidazoline type surfactant may also be preferably used as a foamability improver in addition to the main surfactant.

Besides the above-described components, ingredients commonly used in the classical cleanser or detergent compositions, for example, oily substances, thickeners, wetting agents, colorants, touch improvers, perfume bases, antiphlogistics, germicides, ultraviolet absorbents and the like, may be used so far as no detrimental influence is thereby imposed on the effects of the present invention.

The cleanser compositions according to the present invention can be widely used, for example, as skin cleansers such as facial soap, body soap and solid soap, shampoos, tableware detergents, contact lens detergent, tooth paste, massage cream and the like.

EXAMPLES

Having generally described this invention, a further understanding can be obtained by reference to certain specific examples which are provided herein for purposes of illustrations only and are not intended to be Limiting unless otherwise specified.

In the following examples, all the designations of "part" or "parts" mean part or parts by weight.

Preparation Example 1 of Disintegrating Particles

After kaolin (200 g; product of Wako Pure Chemical Industries, Ltd.) was charged as primary particles into an LFS-GS-2J type high-speed mixer (manufactured by Fukae Kogyo K.K.) and premixed, FIT-3 (sodium carboxymethyl cellulose, $M/C_6=0.9$; 40 g; product of Nippon Paper Co., Ltd.) containing 5% of an active ingredient was gradually added as a binder to conduct granulation. The thus obtained granules were dried at 70° C. for 24 hours and sifted to obtain 45 g of Disintegrating Particles (1) having an average particle diameter of 350 μm.

Preparation Examples 2 to 5 of Disintegrating Particles

Disintegrating Particles (2) to (5) were produced in the same manner as in Preparation Example 1 of Disintegrating Particles except that the kinds and amounts of the primary particles and binder used in Preparation Example 1 were changed as shown in Table 1. Incidentally, "Amount" shown in Table 1 is based on the weight of each active ingredient.

Preparation Example 6 of Disintegrating Particles

UCN-5170D (polyurethane beads; 100 g; product of Dainichiseika Color & Chemicals Mfg. Co., Ltd.) and ground sucrose (100 g; product of Wako Pure Chemical Industries, Ltd.) were charged as primary particles into a SPRAY DRYER SD-1 (manufactured by EYELA Co.), and 5% HPC (hydroxypropyl cellulose; 800 g; product of Wako Pure Chemical Industries, Ltd.) was gradually added thereto to spray dry the resultant mixture. The thus obtained particles were dried further for 24 hours at 70° C. and sifted to obtain 56 g of Disintegrating Particles (6) having an average particle diameter of 400 μm.

Test Example

The average particle diameters and rates of disintegration in water or a salt solution of the disintegrating particles obtained in the preparation examples were measured. The results are shown in Table 1.

(1) Measuring method of average particle diameter:

The measurement was conducted by means of a laser diffraction/scattering type particle size distribution meter LA-910 (manufactured by Horiba Ltd.). A median diameter was used as the average particle diameter.

(2) Measuring method of the rate of disintegration of disintegrating particles:

(Rate of disintegration in purified water, A (%); Rate of disintegation in 10% saline solution, Each sample (0.3 g) of the disintegrating particles was added to purified water (29.7 g) and stored for 15 hours in a thermostatic chamber controlled to 35° C. This specimen was weighed out by 6 g on synthetic leather, and the synthetic leather was massaged with one hand for 1 second (one stroke). Thereafter, the particle diameter of the disintegrating particle sample was measured by means of the laser diffraction/scattering type particle size distribution meter LA-910. The amount of disintegrating particles disintegrated to 80 μm or smaller at this time was expressed in terms of percentage by volume and regarded as the rate of disintegration in purified water, A (%).

The same procedure was conducted with a 10% saline solution to determine the rate of disintegration in 10% saline solution, B (%).

KIM-118: Polyvinyl alcohol, product of Kuraray Co., Ltd.
GL-05: Polyvinyl alcohol, product of The Nippon Synthetic Chemical Industry Co., Ltd.

As is apparent from Table 1, it is understood that in the disintegrating particles according to the present invention, their rates of disintegration in an aqueous solution containing a water-soluble salt is increased in the case where the concentration of the water-soluble salt is low compared to the case where the concentration is high.

Examples 1 to 7 and Comparative Examples 1 to 3

Disintegrating Particles (1) to (6), silica powder (average particle diameter: 210 μm) and CL-5007 (polyethylene beads, product of Sumitomo Seika K.K.; average particle diameter: 360 μm) were separately incorporated to prepare cleanser compositions having their corresponding formulations shown in Table 2. These cleanser compositions according to Examples 1 to 7 and Comparative Examples 1 to 3 were separately used to evaluate their rate of disintegration C, stability to incorporation, cleansing effect, foamability, feeling upon use (massaging effect), itch on the skin and rinsability in accordance with the following respective evaluation methods. The results are shown in Table 3.

(a) Rate of disintegration of disintegrating particles in the cleanser composition (rate of disintegration, C (%)):

Each cleanser composition sample and tap water were weighed out by each 3 g on synthetic leather to conduct

TABLE 1

| Preparation of Example of disintegrating particles | Primary particles | | | | | Particle diameter of disintegrating particles (μm) | Rate of disintegration in purified water, A (%) | Rate of disintegration in 10% saline solution, B (%) |
|---|---|---|---|---|---|---|---|---|
| | Particle | | | Binder | | | | |
| | Kind | diameter (μm) | Amount*1 (wt. %) | Kind | Amount*2 (wt. %) | | | |
| (1) | Kaolin | 5 | 100 | FT-3 | 1 | 150 | 91.7 | 22.9 |
| (2) | W-400G | 30 | 100 | KM-118 | 10 | 300 | 76.4 | 9.2 |
| (3) | W-400G | 30 | 75 | GL-05 | 20 | 350 | 62.6 | 6.8 |
| | PE-1080 | 8 | 25 | | | | | |
| (4) | W-400G | 30 | 25 | KM-118 | 5 | 200 | 88.0 | 18.2 |
| | Sodium Chloride | 21 | 75 | | | | | |
| (5) | Acrylic beads | 9 | 80 | Starch A-55 | 8 | 300 | 80.5 | 12.1 |
| | Starch A-55 | 34 | 20 | | | | | |
| (6) | UCN-5170D | 7 | 50 | HPC | 20 | 400 | 68.3 | 7.5 |
| | Sucrose | 24 | 50 | | | | | |

*1Blending proportion in primary particles.
*2[(Weight of binder)/(weight of primary particles)] × 100.

In the table above, the following definitions apply.

Kaolin: Product of Wako Pure Chemical Industries, Ltd.
W-400G: Cellulose powder, product of Nippon Paper Co., Ltd.
PE-1080: Polyethylene beads, product of Sumitomo Seika K.K.
Sodium chloride: Product of Naikai Engyo Co., Ltd. (guaranteed product).
Acrylic beads: Lauryl acrylate/divinylbenzene 97/7, synthesized product.
Starch A-55: Solfarex A-55, product of Matsutani Kagaku Kogyo Co., Ltd.
UCN-5170D: Fine powder of crosslinked urethane, product of Dainichiseika Color & Chemicals Mfg. Co., Ltd.
Sucrose: Product of Wako Pure Chemical Industries, Ltd.
FT-3: Sodium carboxymethyl cellulose, product of Nippon Paper Co., Ltd.
HPC: Hydroxypropyl cellulose, product of Wako Pure Chemical Industries, Ltd.

model cleansing with one hand for 15 seconds. The cleanser composition was then rinsed out with tap water (300 g). After the whole rinsings were collected and left to stand for 30 minutes, the particle diameter of particles in the rinsings was measured by means of the laser diffraction/scattering type particle size distribution meter LA-910. The rate of disintegration was determined in accordance with the measuring method (2) described above.

(b) Stability to incorporation:

The stability of the disintegrating particles, silica powder or CL-5007 when its corresponding cleanser composition (50 g) was placed in a 100-ml closed vessel and stored for 1 week in a thermostatic chamber controlled to 50° C. was expressed in terms of the rate of disintegration of the particles. The rate of disintegration was determined in accordance with the measuring method (2) described above.

(c) Percent enhancement in cleansing (%):

A solid fat dyed with 1-[(p-phenylazo)-phenyl]azo[2-naphthol] was coated 15 mm across and 0.1 mm thick on synthesized leather, and the thus-coated leather was subjected to a cleansing treatment with each of the cleanser compositions of Examples 1 to 7 and Comparative Examples 1 to 3 containing their corresponding disintegrating particles or other particles, or a cleanser composition in which purified water was incorporated in place of the disintegrating particles or other particles. The solid fat remaining on the synthesized leather was dissolved in an organic solvent, and an absorbance of the resultant solution was measured. This value was compared with a measured value of absorbance on a solution with the solid fat remaining on the synthetic leather not subjected to the cleansing treatment dissolved in the organic solvent, thereby determining the percent enhancement in cleansing. Namely, these absorbance values were substituted into the following equation to determine the percent enhancement in cleansing.

$$W = \frac{W_1 - W_0}{100 - W_0} \times 100(\%)$$

wherein

W=percent enhancement in cleansing;

$W_I$=absorbance of the cleanser composition containing the disintegrating particles or other particles; and $W_0$=absorbance of the cleanser composition containing the purified water.

(d) Foamability:

Each (20 g) of the cleanser compositions and tap water (20 g) were placed in a 120-ml glass container (diameter: 40 mm), and the glass container was shaken 20 times and then left to stand, thereby judging the foamability from the height (mm) of foam after 30 seconds and 5 minutes.

(e) Feeling upon use (massaging effect):

Ten expert women panelists washed their faces with each of the cleanser compositions, thereby evaluating it as to a feeling upon massaging in accordance with the following evaluation standard:

◎: 8 to 10 panelists evaluated it as good;

○: 6 to 7 panelists evaluated it as good;

Δ: less than 5 panelists evaluated it as good;

X: At least one penelists complained a feeling of physical disorder and irritation.

(f): Itch on the skin:

A specified site of the lower arm was subjected to a cleansing treatment each one time in the morning and evening and 14 times in total with each of the cleanser compositions by means of a Teflon applicator. Thereafter, the treated site was visually observed as to desquamation and luster, thereby evaluating the composition in accordance with the following evaluation standard (n=10):

◎: No skin lesion observed;

○: Desquamation visibly developed;

Δ: Desquamation and erythema highly developed;

X: Eruption or pus visibly developed.

(g) Rinsability:

Ten expert women panelists were got to wash their faces with each of the cleanser compositions, thereby evaluating it as to rinsability from whether a feeling of existence of particles was given the panelists when washing or rinsing their faces, in accordance with the following evaluation standard:

◎: 8 to 10 panelists evaluated it as good;

○: 6 to 7 panelists evaluated it as good;

Δ: Less than 5 panelists evaluated it as good;

X: At least one panelists complained a feeling of physical disorder and irritation.

TABLE 2

| Component (wt. %) | Example | | | | | | | Comp. Example | | |
|---|---|---|---|---|---|---|---|---|---|---|
| | 1 | 2 | 3 | 4 | 5 | 6 | 7 | 1 | 2 | 3 |
| Disintegrating particles (1) | 10.0 | — | — | — | — | — | — | — | — | — |
| Disintegrating particles (2) | — | 10.0 | — | — | — | — | — | — | — | — |
| Disintegrating particles (3) | — | — | 10.0 | — | — | — | — | 10.0 | — | — |
| Disintegrating particles (4) | — | — | — | 3.0 | — | — | — | — | — | — |
| Disintegrating particles (5) | — | — | — | — | 10.0 | — | 5.0 | — | — | — |
| Disintegrating particles (6) | — | — | — | — | — | 5.0 | — | — | — | — |
| Silica powder | — | — | — | — | — | — | — | — | 10.0 | — |
| CL-5007 | — | — | — | — | — | — | — | — | — | 10.0 |
| MAP20H | 8.6 | 8.6 | 8.6 | 8.6 | 8.6 | 15.0 | 15.0 | 8.6 | 8.6 | 8.6 |
| AMPHITOL 20N | — | — | — | — | — | 6.0 | 6.0 | — | — | — |
| Triethanolamine | 10.7 | 10.7 | 10.7 | 10.7 | 10.7 | 20.0 | 20.0 | 10.7 | 10.7 | 10.7 |
| Stearic acid | — | — | — | — | — | 3.0 | 3.0 | — | — | — |
| Glycerol | — | — | — | — | — | 3.0 | 3.0 | — | — | — |
| Methyl p-hydroxybenzoate | — | — | — | — | — | 0.1 | 0.1 | — | — | — |
| NaCl | 9.0 | 9.0 | 9.0 | 11.0 | 9.0 | 1.0 | 1.0 | 28.0 | — | — |
| KCl | — | — | — | — | — | 1.0 | — | — | — | — |
| Purified Water | Balance | Balance | Balance | Balance | Balance | Balance | Balance | Balance | Balance | Balance |

MAP20H: Lauryl phosphate, Product of Kao Corporation.
AMPHITOL 20N: 35% aqueous solution of lauryldimethylamine oxide, Product of Kao Corporation.
CL-5007: Polyethylene beads, products of Sumitomo Seika K.K.

TABLE 3

| | Stability to incorporation % | Rate of disintegration % | Percent enhancement in cleaning % | Foamability After 30 sec. (mm) | Foamability After 5 min. (mm) | Feeling upon use and massaging | Itch on the skin | Rinsability |
|---|---|---|---|---|---|---|---|---|
| Ex. 1 | 15.3 | 98.5 | 70 | 70 | 65 | ◎ | ◎ | ◎ |
| Ex. 2 | 4.1 | 67.6 | 68 | 70 | 65 | ◎ | ◎ | ◎ |
| Ex. 3 | 6.9 | 72.5 | 67 | 70 | 65 | ◎ | ◎ | ◎ |
| Ex. 4 | 14.1 | 81.0 | 53 | 65 | 55 | ○ | ◎ | ◎ |
| Ex. 5 | 9.0 | 78.5 | 62 | 70 | 65 | ○ | ◎ | ◎ |
| Ex. 6 | 8.7 | 75.6 | 65 | 75 | 72 | ◎ | ◎ | ◎ |
| Ex. 7 | 13.2 | 85.3 | 65 | 75 | 73 | ◎ | ◎ | ◎ |
| Comp. Ex. 1 | 2.8 | 64.8 | 48 | 8 | 2 | ○ | △ | ◎ |
| Comp. Ex. 2 | 0 | 0 | 61 | 75 | 40 | ○ | × | × |
| Comp. Ex. 3 | 0 | 0 | 68 | 75 | 40 | ◎ | △ | △ |

As is apparent from Table 3, it is understood that the disintegrating particles in the cleanser compositions according to the present invention have high stability to incorporation in the storage test at 50° C., disintegrate during cleansing and rinsing and possess excellent rinsability. In addition, the cleanser compositions have high percent enhancement in cleansing upon use, give users a pleasant feeling upon use (massaging) and cause no itch on the skin. Further since the concentration of the water-soluble salt in the cleanser compositions according to the present invention is lower than its saturated stability, the cleanser compositions retain extremely high foamability compared with the cleanser composition containing the water-soluble salt at a concentration higher than its saturated solubility in Comparative Example 1, and so have excellent cleanability and give users a pleasant feeling upon use.

INDUSTRIAL APPLICABILITY

The cleanser compositions according to the present invention have excellent physical (mechanical) cleanability and stability over time and give users a pleasant feeling upon use. In addition, the compositions cause little damage to and itchiness of the skin because the disintegrating particles are disintegrated during cleansing and rinsing. The particles have excellent rinsability properties because they are readily disintegrated during rinsing.

This application is based on Japanese Patent Application No. 26371/1997 filed on Sept. 29, 1997, the entire contents of which are hereby incorporated by reference.

Obyiously, numerous modifications and variations of the present invention are possible in light of the above teachings. It is therefore to be understood that, within the scope of the appended claims, the invention may be practiced otherwise than as specifically described herein.

What is claimed is:

1. A disintegrating particle, comprising:
   i) primary particles, wherein at least a portion of the primary particles are insoluble in water, wherein said primary particles which are insoluble in water are selected from the group consisting of polyethylene, polypropylene, polyamide, polyethylene terephthalate, polystyrene, polyurethane, sodium poly(meth)acrylate, poly(meth)acrylic esters, rubbers, and cross-linked derivatives thereof or selected from the group consisting of chitosan, fruit shells, bentonite, talc, mica, kaolin, sepiolite, silica, calcium carbonate, titanium oxide, silicic acid anhydride, hydroxy calcium apatite and pearl powder; and
   ii) a water soluble binder, wherein
      said primary particles are agglomerated by said water soluble binder, the average particle diameter of the primary particles is at most 70 μm, the average particle size of said disintegrating particle ranges from 150 to 360 μm, the rate of disintegration of the disintegrating particle in 10% saline solution is 6.8% to 22.9%, and
      at least 60 vol. % of the particles are disintegrated in an aqueous solution containing sodium chloride at a concentration lower than 1.5% wt. %.

2. The disintegrating particle of claim 1, wherein the primary particles are water-insoluble or contain a mixture of water-insoluble particles and water-soluble particles.

3. The disintegrating particle of claim 1, wherein the content of the water-soluble binder is 0.5 to 30 wt. % based on the weight of the primary particles.

4. The disintegrating particle of claim 1, wherein said concentration is 1.0 wt % or less.

5. The disintegrating particle of claim 1, wherein the primary particles comprise kaolin.

6. The disintegrating particle of claim 5, wherein the primary particles further comprise starch or a derivative thereof.

7. The disintegrating particle of claim 6, wherein the primary particles further comprise cellulose or a derivative thereof.

8. The disintegrating particle of claim 5, wherein the primary particles further comprise cellulose or a derivative thereof.

9. The disintegrating particle of claim 1, wherein the primary particles further comprise starch or a derivative thereof.

10. The disintegrating particle of claim 1, further comprising primary particles which are in-soluble in water selected from the group consisting of cellulose, starch and a mixture thereof.

11. A cleanser or detergent composition comprising the disintegrating particle of claim 1, a water-soluble salt, a surfactant and water, wherein the water-soluble salt is an inorganic salt, and the inorganic salt is present at a concentration of from 1.5 wt. % to less than the saturated solubility of the inorganic salt.

12. The composition of claim 11, wherein said concentration is 1.0 wt % to less than the saturated solubility.

13. The composition of claim 11, which comprises 1 to 25 wt. % of the disintegrating particles.

14. The composition of claim 11, wherein at least a portion of the disintegrating particles disintegrate during the cleansing and rinsing of an object.

15. The composition of claim 11, wherein at least a portion of the disintegrating particles disintegrate during the cleansing and rinsing of an object, and the rate of disintegration to particles having an average particle diameter of 80 µm or smaller is at least 60 vol. %, based on the total volume of the disintegrating particles.

16. A method of cleaning an object, comprising contacting the object with the composition of claim 11, followed by rinsing.

17. The method of claim 16, wherein the object is human skin.

18. A cleanser or detergent composition comprising the disintegrating particle of claim 10, a water-soluble salt, a surfactant and water, wherein the concentration of said water-soluble salt is lower than its saturated solubility.

19. The composition of claim 18, wherein said concentration is 1.0 wt. % to less than the saturated solubility.

20. The composition of claims 18, which comprises 1 to 25 wt. % of said disintegrating particles.

21. The composition of claim 18, wherein at least a portion of said disintegrating particles disintegrate during the cleansing and rinsing of an object.

22. A method of cleaning an object, comprising contacting an object with the composition of claim 18, followed by rinsing.

23. The method of claim 22, wherein said object is human skin.

* * * * *